United States Patent

Zimmer et al.

[11] Patent Number: 5,814,522
[45] Date of Patent: Sep. 29, 1998

[54] MULTILAYER ANALYTICAL ELEMENT FOR THE DETERMINATION OF AN ANALYTE IN A LIQUID

[75] Inventors: Volker Zimmer, Ludwigshafen; Heinz Macho, Fürth; Rolf Lerch, Ilvesheim, all of Germany

[73] Assignee: Boeringer Mannheim GmbH, Mannheim, Germany

[21] Appl. No.: 668,059

[22] Filed: Jun. 20, 1996

[30] Foreign Application Priority Data

Jun. 24, 1995 [DE] Germany ............ 195 23 049.3

[51] Int. Cl.⁶ .................................. G01N 33/48
[52] U.S. Cl. .................. 436/170; 436/169; 422/56; 422/57; 422/58
[58] Field of Search .................. 422/56–58, 61; 436/164, 169, 170

[56] References Cited

U.S. PATENT DOCUMENTS

| | | | |
|---|---|---|---|
| 4,292,272 | 9/1981 | Kitajima et al. | 422/57 |
| 4,816,224 | 3/1989 | Volgel et al. | 422/55 |
| 5,055,195 | 10/1991 | Trasch et al. | 210/638 |
| 5,104,811 | 4/1992 | Berger et al. | 436/164 |
| 5,314,803 | 5/1993 | Wilk et al. | 422/58 |

FOREIGN PATENT DOCUMENTS

| | | |
|---|---|---|
| 0166365 | 1/1986 | European Pat. Off. |
| 9217768 | 10/1992 | WIPO |

OTHER PUBLICATIONS

The Condensed Chemical Dictionary, tenth edition, p. 650, 1981.

*Primary Examiner*—Lyle A. Alexander
*Attorney, Agent, or Firm*—Fulbright & Jaworski

[57] ABSTRACT

A sample application zone and detection zone are arranged on a pile-like complex made of a fleece and a porous membrane which are in a direct or indirect contact that enables passage of liquid through the contact area and the membrane is a polyamide, polyvinylidene difluoride, polyether sulfone or polysulfone membrane which transports liquid significantly slower over the area than the fleece.

9 Claims, 2 Drawing Sheets

MULTILAYER ANALYTICAL ELEMENT FOR THE DETERMINATION OF AN ANALYTE IN A LIQUID

BACKGROUND OF THE INVENTION

The invention concerns a multilayer analytical element for the determination of an analyte in a liquid containing a sample application zone and a detection zone arranged side by side in which the detection zone contains a reagent which forms a detectable signal with the analyte to be determined or with a substance derived therefrom. In addition the invention concerns a pile-like material complex which is composed of a fleece and a porous membrane as well as the use of such a pile-like material complex to manufacture a multilayer analytical element. An additional subject matter of the invention is a method for the determination of an analyte in a liquid by means of a multilayer analytical element.

A multilayer analytical device is known for example from U.S. Pat. No. 4,292,272 in which the sample application and detection zones are arranged in one axis above one another. A hydrophilized spreading layer made of fabric is laminated in this device on a layer containing reagent. This layer containing reagent is a film of gelatin, polyvinyl alcohol, polyvinyl pyrolidone, agarose, sodium polyvinylbenzenesulfonate and the like. Considerable know-how is necessary to manufacture such film layers and thus it is not surprising that this technology was developed above all by companies from the photographic film industry and is still used today there. The manufacture of such analytical devices has a high assembly risk since all reagents are processed together with the film solution or suspension. In order to examine coloured liquids it is often necessary to use additional optical barrier layers to prevent the colour of the liquid from interfering with the detection side which is opposite to the sample application side.

Multilayer analytical elements are described in WO-A-9217768 in which two or more layers of a porous paper or polymer material are held together by an intervening layer. At least one of the layers contains reagent which has been incorporated into the layer before the layers have been joined together. Only test devices with paper as the layer materials are described in more detail. The exact nature of potential polymer materials is not stated. Insofar horizontal as well as vertical liquid transport occurs in parallel to a considerable extent in the proposed test devices when the liquid passes from one layer into another without a significant separation with respect to space and time. As a consequence reagent in the layer which contains it is dissolved by the sample liquid front and is cotransported. Usually more substance is dissolved in the liquid front than in the following liquid. This is also called a chromatography effect. In the case of very rapid reactions the analyte to be detected already reacts in the liquid front. The sample then becomes depleted of analyte over the path length of the layer to be filled with liquid. Both effects lead to an inhomogeneous signal generation.

EP-A-0 271 854 concerns a multilayer analytical element for the analytical determination of components of body fluids in which an application, a detection and an absorptive zone are located side by side on a support layer. The application zone is connected to the absorptive zone by a capillary active transport path. A fleece or fabric are mentioned as possible examples for the material of the transport path. Polyamide is described as being particularly suitable. The transport path extends from the beginning of the application zone to beyond the detection zone. One or several reaction layers are arranged in the detection zone in such a manner that they are in liquid contact with a liquid transported in the transport path. The reaction layer can lie directly on the layer forming the transport path. It can be composed of paper, fleece, gel, gelatin or a porous plastic material. According to the European Application the absorption power, absorption volume and absorption rates of the layers should be matched in such a way that liquid is available in the transport layer of the detection zone until the reaction layers have taken up a defined amount of liquid but that afterwards liquid contact between the reaction and transport layer is interrupted by the action of the absorption zone. In this process the liquid is absorbed out of the transport path. From the example it is apparent that the reaction layers are treated with reagent before assembly. As a result there is also an assembly risk in this case since, if the assembly of the layers treated with expensive reagent is faulty, intermediate products manufactured at high costs are lost. Matching the properties of the materials of all function zones is quite complicated due to the high number of function zones. In addition the continuous flow of liquid in the transport path needed to fill the reaction layer and to subsequently terminate the liquid contact between the transport layer and the reaction layer results in flow-dependent disturbances in the signal generation of the reaction layer. Thus one can not expect a colour reaction which is areally homogeneous.

SUMMARY OF THE INVENTION

The object of the invention was therefore to provide compact, simple and universal analytical elements that are cheap to manufacture in which a reaction occurs homogeneously over the whole area in the reaction layer without chemically immobilizing the reagent present there.

The invention concerns a multilayer analytical element for the determination of an analyte in a liquid containing a sample application zone and a detection zone arranged side by side in which the detection zone contains a reagent which forms a detectable signal with the analyte to be determined or a substance derived therefrom characterized in that the sample application zone and detection zone are arranged on a pile-like complex made of a fleece and a porous membrane which are in a direct or indirect contact that enables an areal passage of liquid and the membrane is a polyamide, polyvinylidene difluoride, polyether sulfone or polysulfone membrane which transports liquid horizontally, i.e. over the area, considerably more slowly than the fleece.

The invention also concerns a pile-like material complex composed of a fleece and a porous membrane characterized in that the membrane is a polyamide, polyvinylidene difluoride, polyether sulfone or polysulfone membrane which transports liquid horizontally, i.e. over the area, considerably more slowly than the fleece.

In addition the invention concerns the use of one of the pile-like material complexes as described above to manufacture an above-mentioned analytical element according to the invention.

Finally the invention concerns a method for the determination of an analyte in a liquid by means of an analytical element according to the invention which is characterized in that the liquid to be examined is contacted in the sample application zone with the fleece and is determined on the membrane side as a result of a signal generation in the detection zone.

In the multilayer analytical element according to the invention the sample application zone and the detection zone are arranged side by side which means that they are laterally offset and not arranged in the axis of gravity. The term zones encompasses the overall analytical element and can—from the vertical perspective—pass through several layers. According to the invention the multilayer analytical element of the present invention contains a pile-like complex of a fleece and a porous membrane. The sample application zone and detection zone therefore extend—from a vertical perspective—through the fleece as well as through the membrane.

In the sample application zone the liquid sample to be examined is contacted with the multilayer analytical element. A signal is measured in the detection zone of the multilayer analytical element if an analyte is located in the liquid to be examined.

According to the present invention the fleece and porous membrane must be in a direct or indirect contact enabling an areal passage of liquid. A direct contact can be achieved by manufacturing the porous membrane on the fleece or conversely manufacturing the fleece on the porous membrane. In order to ensure an adequate contact between the fleece and membrane materials which have been previously separately manufactured they can also be held together by clips, sewing or glueing the edges. However, it is also possible to bring the previously manufactured fleece and membrane into a permanent indirect contact with one another by means of a further material. Such a material can be an adhesive such as for example a melt adhesive which is applied in the thread-like or point-like manner in such a way that it allows liquid to pass essentially unimpeded between the fleece and membrane layer. Such adhesive layers are for example known from EP-A-0 166 365. It is also possible to place thermoplastic fabrics or fleeces between the fleece and membrane in such a way that after thermal treatment the fleece and membrane are laminated in such a way that an areal liquid passage between the fleece and membrane is possible. Such a process is for example known from WO-A-9217768. Potential thermoplastic materials are also listed in this patent application. According to the invention it has proven to be preferable to laminate the fleece and porous membrane by means of a thin net of thermoplastic polyamide copolymer. The thermoplastic polyamide copolymer is advantageously one which melts or becomes soft at temperatures of more than 100° C. and particularly preferably between 100° and 120° C. such as for example Xiro®-Web from the Sarnatech-Xiro AG Company (Schmitten, Switzerland).

A further possibility of producing a flat complex of fleece and membrane is to spray on adhesive polymers as melts or solutes in such a way that a large part of the contact surface remains open. The second material must be placed on optionally under pressure before hardening. In this process an irregular adhesive structure is formed on the contact surface.

The manner in which the fleece and the porous membrane of the pile-like complex according to the invention are laminated and what material is used for this are only of secondary importance provided that it is ensured that the material holding the two layers together is chemically inert and leads to a contact between the fleece and porous membrane which ensures a homogeneous areal passage of liquid from the fleece into the porous membrane. The properties of the fleece and the porous membrane of the pile-like material complex are much more important.

The fleece must be able to transport liquid very rapidly over the area. Cellulose or glass fibre fleeces have proven to be suitable. Glass fibre fleeces are especially suitable when the sample to be examined is whole blood. Glass fibre fleeces as they are for example described in the European Patent Application 0 045 476 are excellently suitable. These are above all glass fibre fleeces made of glass fibres with an average diameter of 0.2 to 2.5 $\mu$m and a density of 0.1 to 0.5 g/cm$^3$. In such glass fibre fleeces the erythrocytes of a blood sample migrate more slowly than the plasma which ultimately leads to a separation of erythrocytes and plasma. In order to further improve the separation of the plasma in the fleece material, it can also carry substances that aggregate erythrocytes. Such substances are known to a person skilled in the art. Thus for this purpose one can for example use lectins, antibodies against erythrocytes, amino acids or even dyes and aliphatic diamines such as those which are for example known from the European Patent Application 0 133 895 or cationic polymers.

According to the invention a porous material can be used as the membrane which transports liquid over the area considerably more slowly than the fleece. This means that in the case of a direct or indirect areal contact between the fleece and membrane the liquid which is applied to the fleece spreads in it very rapidly before it ascends vertically and uniformly over the contact area into the membrane and fills it. Membranes in the present sense are understood as thin, continuous but nevertheless porous layers. Polyamide, polyvinylidene difluoride, polyether sulfone or polysulfone membranes are particularly preferred according to the invention. Polyamide membranes are very specially preferred in particular those made of polyamide 66. In such membranes which can be used according to the invention the wetting over the area is relatively slow so that the transport rate of liquid over the area of the membrane is also relatively slow. Membranes that can be used according to the invention can also have supporting fleeces or fabrics made of other materials in the inside in order to improve their mechanical properties such as resistance to tearing or wet-expansion.

Polysulfone, polyether sulfone and polyvinylidene difluoride membranes can in general then be used advantageously when they are activated so as to be wettable since they are naturally hydrophobic. This activation to make them wettable can for example be achieved by alloying with a water-soluble or water-swellable polymer during the membrane manufacturing process. Polyvinyl pyrolidone can for example be used for this.

The membranes used according to the invention should have pores with a pore diameter between 0.01 and 5 $\mu$m, preferably between 0.04 and 3 $\mu$m. Those membranes have proven to be particularly preferred which are composed of two layers which, however, are so closely joined together that they cannot be separated from one another. Both layers differ in their pore size. One of the layers has small pores the other has larger pores. In the small-pored layer of the membrane the pore size is 0.01 to 1$\mu$m, preferably 0.04 to 0.5$\mu$m. In the region with the larger pores the pore size is 0.1 to 5$\mu$m, preferably 0.3 to 3$\mu$m. The pore size in the large-pored region is at least 3-fold and preferably 5- to 10-fold larger than that of the small-pored region of the membrane. In the multilayer analytical element according to the invention such a membrane which has pores of different pore sizes on opposite surfaces is arranged such that the membrane surface with the large pores faces the fleece.

The term "pore diameter" indicates that particles above a size which corresponds to the pore diameter cannot penetrate through the layer during a filtration process.

In order to increase the wettability of the membrane by the liquid which enters the membrane from the fleece, the membrane can be treated with wetting agents. Detergents or water-insoluble proteins come into consideration for this. Polyvinylidene difluoride, polyether sulfone and polysulfone membranes treated with wetting mediators can be used according to the invention to particular advantage.

In the total sample application zone which extends up to the detection zone of the multilayer analytical element the membrane is treated such that it cannot take up or transport liquid. This can for example be achieved by applying polymers to this zone in such a way that the membrane pores are closed thus preventing liquid from passing from the fleece into the membrane. Basically all polymers are suitable for this which are water-insoluble after being applied to the membrane. Hydrophobic polymers can be used in particular to prevent liquid uptake into the membrane in the sample application zone. An example of such a possible polymer is a copolymer of vinyl acetate and vinyl laurate.

The sample application zone of the multilayer analytical element according to the invention is especially preferably treated with a material that prevents liquid uptake in such a way that not only the membrane in the sample application zone contains this material but also the contact zone between the membrane and the fleece. This is intended to prevent liquid within the sample application zone of the multilayer analytical element from being able to move in the contact zone between the membrane and fleece. This could for example interfere with the use of the multilayer analytical element according to the invention for examining blood as the sample liquid. Therefore sample liquid should not come into contact with the membrane in the sample application zone of the multilayer analytical element according to the invention. In order to achieve this it is sufficient when only the upper part of the fleece which is nearest to the membrane is treated with material that prevents liquid uptake in the sample application zone. For practical reasons it has, however, proven to be advantageous when the entire cross-section of the membrane in the sample application zone, the entire contact zone between the fleece and membrane in the sample application zone as well as the region of the fleece which is nearest to the membrane in the sample application zone are treated with material that prevents liquid uptake.

In the multilayer analytical element according to the invention the membrane must be also designed in such a way that it can carry the reagent required for the analyte determination. This means that it must be inert towards this reagent but should absorb it. A covalent binding of the reagent to the membrane is not necessary but also not excluded. However, due to the uniform passage of liquid over the entire area of the detection zone from the fleece into the membrane it is adequate when the reagent necessary for the analyte determination is adsorbed there in such a way that it generates the necessary signal with the analyte for the analyte determination.

In particular colour change, colour formation or decrease in colour come into consideration for the signal formation. However, reagents can also be used which generate fluorescence or decrease fluorescence in the presence of the analyte. Colour formation or colour change are, however, the preferred method of signal generation. Suitable reagents that depend on the analyte are known to a person skilled in the art for this.

The reagent is located on the part of the membrane which extends into the detection zone of the multilayer analytical element according to the invention. Although the reagent can in principle be contained within the entire cross-section of the membrane, the reagent is preferably applied on or in the membrane in such a way that the reagent is located on the side of the membrane which faces away from the fleece. Ideally the surface of the membrane adjacent to the fleece is free of reagent.

While it is possible for the determination of an analyte that reagent is contained in the entire outer surface of the membrane that is located in the detection zone, it is also possible to limit this reagent in the membrane to only part of the detection zone. Thus it is also possible to accommodate several different reagents next to one another in the detection zone of the membrane in order to determine several analytes in a liquid sample. In such a case the specific test zones for different analytes can be present separate from one another within the detection zone i.e. they are not contiguous but are separated from one another by reagent-free areas or they can be in such close proximity that they touch one another. In particular in the case of such a multilayer analytical element according to the invention which is suitable for the determination of several analytes in a liquid it has proven to be advantageous that the arrangement according to the invention substantially prevents a horizontal chromatography of the liquid in the membrane by i.e. migration of the liquid in the membrane surface. Due to the fact that liquid spreads rapidly in the fleece and then subsequently passes homogeneously into the membrane over the area of the contact zone between the fleece and membrane, there is no mixing of the reagents in the test zones for the various analytes arranged side by side.

In some circumstances several reaction steps may be necessary to determine an analyte and the reagent necessary for this may contain substances which are not compatible with one another or for other reasons it may be necessary to spatially separate the reagent components. In such a case it is possible to place only those reagent components in the membrane that form a detectable signal with a substance derived from the analyte to be determined. The other reagent components can then for example also be contained in the fleece or applied thereto in such a way that the analyte is firstly converted there into a substance derived from the analyte and this then leads to a formation of a detectable signal only in the membrane. Thus for example it is conceivable that for example triglycerides are cleaved in a pre-reaction occurring in the fleece in such a way that glycerol as the substance derived from triglyceride leads to a detectable signal in the membrane which correlates with the amount of triglyceride in the sample.

Equally it is also possible to carry out interference elimination reactions in the fleece such as for example the removal of ascorbic acid in the sample liquid by reagent components contained in the fleece such as iodate or ascorbate oxidase. Stability may also be the deciding factor for using reagent components that are spatially separated in the fleece and membrane. The reagent components that are present in the fleece can then accumulate in the sample liquid and be cotransported into the detection zone where all the reagent components necessary for the analyte detection are then present so that the detection reaction starts and proceeds there.

Due to the advantageous properties which the pile-like material complex of fleece and porous membrane that is described above offers, this pile-like material complex is also intended to be a subject matter of the invention.

As already described above the pile-like material complex can be used to manufacture a multilayer analytical element according to the invention. For this purpose the pile-like material complex can optionally be made easier to handle by for example mounting it on a stiff supporting foil so that the pile-like material complex can be easily and hygienically contacted with the sample to be examined. The supporting foil can be adjacent to the membrane so that sample liquid can be applied to the freely accessible sample application zone of the fleece. In order to measure the detection zone in the membrane it is necessary that in such a case the supporting foil is perforated or transparent in the detection zone. In the case of holes these should of course be at the site at which the zones or test zones containing the reagent are located. Correspondingly the size of the holes must be matched to the size of the test zone.

A multilayer analytical element according to the invention can, however, also be envisaged in which the pile-like material complex made of the fleece and porous membrane is in a solid housing which is made for example of plastic. This housing must have at least one aperture through which the sample liquid can be contacted with the sample application zone. As described above for the supporting foil in the case of the housing the part adjacent to the membrane can also be transparent or perforated at least in the area of the detection zone.

In a multilayer analytical element according to the invention the sample can be applied directly to the sample application zone. However, embodiments may be present in which the liquid is firstly not contacted directly with the sample application zone but has to firstly reach this after passing through a particular path for example a capillary channel.

After liquid has contacted the fleece of the pile-like material complex according to the invention in the sample application zone, the liquid spreads rapidly over the entire area of the fleece that is accessible to the liquid. When the fleece contains liquid, liquid penetrates evenly i.e. homogeneously over the entire area into the membrane lying above. Since liquid is transported significantly more slowly in the membrane area than in the fleece area, the filling of the membrane area with liquid is mainly dependent on the transversal passage of liquid from the fleece into the membrane that is intended to spread the liquid over the area. If this passage of liquid from the fleece into the membrane is not possible due to a water impermeable layer in the sample application zone, liquid can only pass in the detection zone. Here the sample liquid comes into contact with the reagent or reagents in the test zone or test zones of the membrane upon which a signal is formed in the test zones which is observed visually or by an instrument when the analyte or analytes to be determined are present. If blood is used as the sample liquid and an appropriate selection is made of the fleece material such as for example glass fibres or appropriate use is made of substances that aggregate erythrocytes in the sample application zone of the fleece, erythrocytes and plasma are separated in the fleece so that only plasma reaches the test zones located in the membrane in the detection zone of the multilayer analytical element.

DETAILED DESCRIPTION OF THE PREFERRED EMBODIMENT

Figure 1:
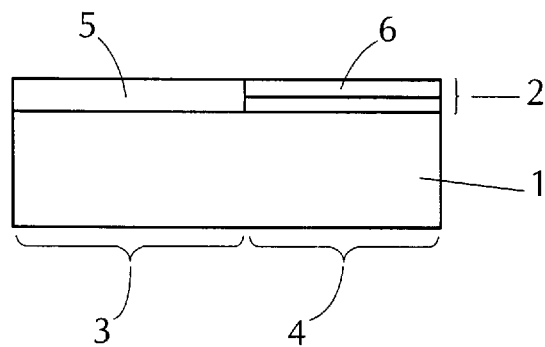
FIG. 1 shows an embodiment of a pile-like material complex in an analytical element according to the invention.

A preferred pile-like material complex of fleece (1) and membrane (2) according to the invention is shown in FIG. 1. The sample application zone (3) extends over the area that is defined by the liquid impermeable area (5) of the membrane (2). In this manner liquid which is applied to the fleece in the sample application zone (3) is in any case prevented by the liquid impermeable area (5) from penetrating into the membrane (2) at this site. A passage of liquid from the fleece (1) into the membrane (2) is only possible within the detection zone (4). As a result of the selection of materials described above liquid applied to the fleece (1) in the sample application zone (3) distributes rapidly within the fleece (1) and from there it reaches the detection zone (4) of the membrane (2) at right angles to the spreading direction within the fleece area and from there it enters into zone (6) containing the reagent. If the analyte is present a signal is formed there which can be observed visually or by an instrument from the membrane side.

Figure 2:
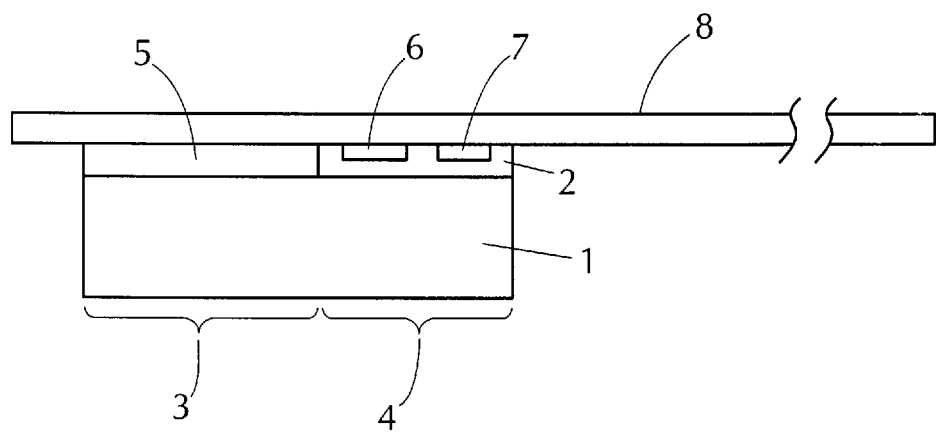
FIG. 2 shows a possible embodiment of a multilayer analytical element according to the invention.

An embodiment of a multilayer analytical element is shown in FIG. 2 in which the pile-like material complex of fleece (1) and membrane (2) is attached to a stiff support foil (8). All possible inert stiff materials come into consideration as stiff support foils which facilitate the handling of the material complex. Possible materials can be glass, cardboard or plastic. Stiff plastic foils are particularly preferred.

In the multilayer analytical element according to the invention shown in FIG. 2 two areas (6, 7) containing reagent are shown in the membrane (2) which enable two different analytes to be detected in the sample liquid to be examined. In the case shown the support foil (8) in the detection zone is not perforated and must therefore be transparent in this area in order to observe a signal formation in the detection zone (4) of the membrane (2) in the region of the test zones (6, 7).

Figure 3:
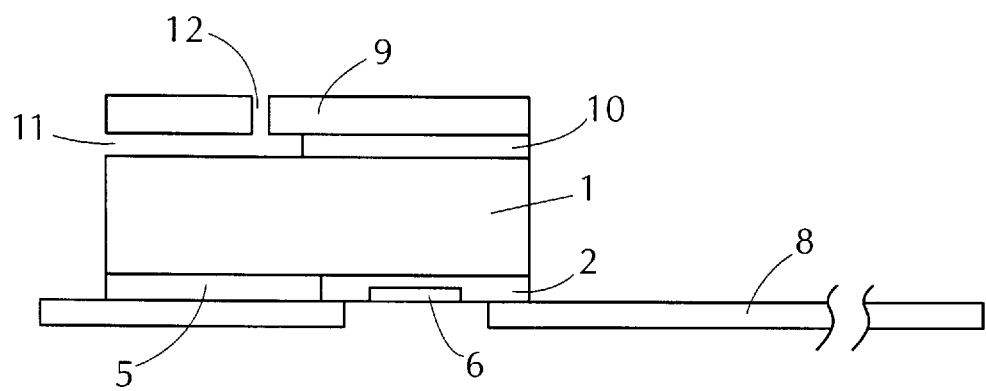
FIG. 3 shows a further possible embodiment of a multilayer analytical element according to the invention.

A further possible embodiment of a multilayer analytical element according to the invention is shown in FIG. 3. In this case the pile-like material complex of fleece (1) and membrane (2) is located on a support foil (8) which has a hole in the area of the test zone (6) containing reagent. A covering foil (9) is attached with a spacer (10) on the fleece side in such a way that there is a capillary gap (11) in the sample application zone.

Inert adequately stiff materials can be used as the covering foil (9) such as plastic foils. In the case of the material for the spacer (10) it is also important that it is inert towards the sample liquid and the analyte. In addition the covering foil (9) as well as the spacer (10) should not take up liquid or the analyte. To this extent materials that are suitable for this purpose should not be absorbent.

If the capillary gap (11) is contacted with sample liquid, liquid rapidly fills the entire capillary gap (11). In this process air can escape from the air outlet (12). Liquid passes from the capillary gap (11) into the sample application zone of the fleece (1) and rapidly spreads there. Due to the liquid impermeable area (5) in the membrane (2) and due to the fleece surface adjacent to the membrane, liquid can only pass from the fleece (1) into the membrane (2) in the area of the detection zone and form a signal there in the test zone (6) when the analyte to be determined is present in the sample liquid which can be observed visually or by an instrument. If the capillary gap (11) is open on the side an air outlet (12) is not absolutely necessary. A vent (12) is only necessary in the case of a channel (11) which is only open at the inlet side.

Figure 4:
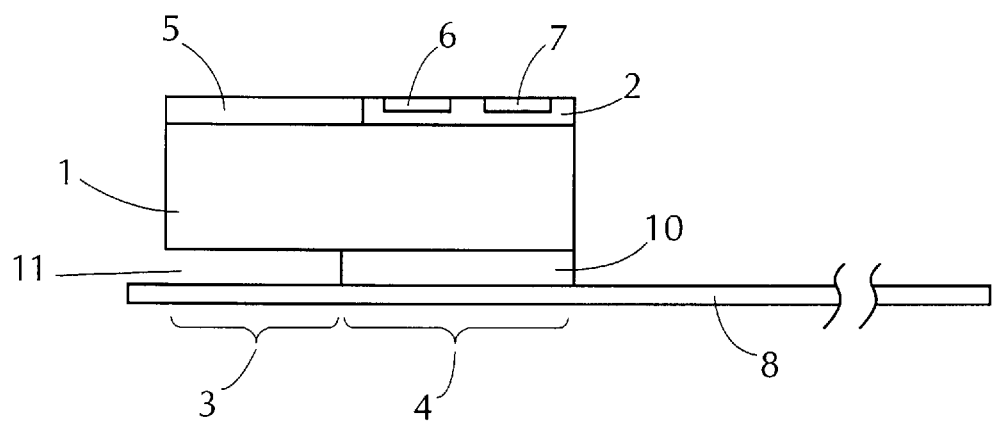
FIG. 4 shows an alternative embodiment for a multilayer analytical element according to the invention.

FIG. 4 shows an alternative preferred embodiment of a multilayer analytical element according to the invention. In this case the pile-like material complex of fleece (1) and membrane (2) is attached to the support foil (8) by means of a spacer (10). Measurements are carried out on the freely accessible membrane (2).

Using the described pile-like material complex according to the invention or the multilayer analytical element according to the invention it is possible to carry out a reaction which is homogeneous over the whole area in a reaction layer without chemically immobilizing the reagents. The combination of a fleece that rapidly transports liquid and a porous membrane which takes up liquid homogeneously from the fleece over the entire area avoids the chromatography effects that occur in the state of the art that are due to a concentration of reagents in a liquid front. In addition the effect that an analyte in a liquid front reacts faster and thus more strongly than in the liquid which follows behind is also avoided.

The multilayer analytical element according to the invention is compact, simple and cheap to manufacture. In a stepwise manufacturing process it is possible to firstly manufacture the pile-like material complex before expensive reagents are applied. Thus the cost risk that a mistake occurs during the assembly of the material complex is minimized compared to the hitherto conventional processes in which each layer is assembled ready to use possibly containing expensive reagents. Due to the fact that the pile-like material complex can be used without reagent as a semi-finished product in such a way that it is not treated with the reagents required for the respective analyte determination until after completion, the reagent-free material composite can be used universally.

A multilayer analytical element according to the invention can be manufactured by firstly producing a composite of fleece and membrane. The combination can be carried out by laminating the fleece and membrane together by clips, glueing the edges, sowing or by an intermediate thermoplastic layer. Subsequently the sample application zone of the membrane of the material composite can be treated in such a way that the membrane and the layer of the fleece adjacent to the membrane is made impermeable to the sample liquid. This can for example be achieved by a non-saturating impregnation of this membrane region by means of a plastic solution, emulsion or suspension. In such a case care must be taken that the solvents or dispersants do not adversely affect the membrane, the fleece or the bonding of both materials. Although this of course is in principle also already possible before laminating the fleece with the membrane, it is more advantageous to coat the fleece in the sample application zone with substances such as wetting agents, erythrocyte-aggregating substances, substances which reduce interference in the detection reaction or reagent components which are not compatible with the other reagent components using non-saturating impregnation methods after laminating the fleece and membrane. In the detection zone of the membrane the reagents for the determination of the analyte or analytes are also applied to the material complex as a non-saturation impregnation. The application or incorporation of substances using non-saturating impregnation processes is carried out in defined areas i.e. after the process is completed the substances are only present in certain areas of the fleece or membrane but not in the entire material. The non-saturation impregnation processes enable the penetration depth of the substances to be regulated. Thus it is possible to limit the reagents to the fleece or to the membrane of the material composite. Non-saturation impregnation processes are for example print processes such as silk printing, jet impregnation, spraying, ink-jet or line impregnation processes with a roller. Especially the roller process can be used advantageously to manufacture the multilayer analytical element according to the invention. In this process part of a roller runs through the liquid which it is intended to apply to the material complex. The material complex itself is contacted by means of a supporting roller with the application roller that runs through the impregnation solution in such a way that the application roller is kept moving by the material complex passing through. Thus when the application roller rolls off on the material complex, liquid is applied to the fleece or membrane over the width of the application roller. Subsequently the treated material complex is dried and can then be cut so that it can be inserted into a plastic housing in order to manufacture the multilayer analytical element. It is, however, also possible to additionally apply a supporting foil onto the membrane before cutting the material complex manufactured as described above. A subsequent cutting of the material complex at right angles to the direction of travel of the band of the material complex thus results in ready-to-use multilayer analytical elements.

We claim:

1. Multilayer analytical element for the determination of an analyte in a liquid, said multilayer analytical element comprising an application zone and a detection zone arranged side by side on a stacked complex composed of a fleece and a porous polyamide, polyvinylidene difluoride, polyether sulfone or polysulfone membrane which transports liquid more slowly over its area than said fleece, wherein said fleece and said porous membrane are in fluid contact, via a contact area which permits passage of liquid therethrough, a portion of said porous membrane being in said detection zone and having a detection reagent in it or on it, which forms a detectable signal with said analyte.

2. Multilayer analytical element as claimed in claim 1 wherein the membrane is composed of a small-pore and a large-pore layer which are arranged with the large pore layer facing the fleece.

3. Multilayer analytical element as claimed in claim 1, wherein reagent is located in or on the membrane at a site at which the membrane can take up liquid.

4. Multilayer analytical element as claimed in claim 1, wherein the pores of the membrane have a pore size between 0.01 and 5 µm preferably between 0.04 and 3 µm.

5. A method for determining an analyte in a liquid, comprising contacting said liquid to the multilayer analytical element of claim 1, and determining signal formed as a determination of said analyte.

6. Multilayer analytical element as claimed in claim 1, wherein the membrane is treated in the sample application zone in such a way that it does not take up any liquid.

7. Multilayer analytical element as claimed in claim 6, wherein the membrane contains reagents for the determination of different analytes which are spatially separated from one another.

8. Method for determination of a analyte in a liquid, comprising contacting said liquid to a multilayer analytical element which has a sample application zone and a detection zone arranged side by side, said multilayer analytical element comprising a fleece and a porous polyamide, polyvinyl difluoride, polyether sulfone or polysulfone membrane, each of which transports liquid, said porous membrane transporting liquid more slowly than said fleece, wherein a portion of said porous membrane is in said detection zone, and contains a reagent which forms a signal with said analyte and is in fluid contact with said fleece, said fluid contact permitting passage of liquid from said fleece to said porous membrane, said porous membrane, and determining formation of said signal as determination of said analyte.

9. Multilayer analytical element for determination of an analyte in a liquid sample, said multilayer analytical element comprising a sample application zone and a detection zone arranged side by side, said multilayer analytical element comprising a fleece which transports said liquid sample and a porous polyamide, polyvinylidene difluoride, polyether sulfone, or polysulfone membrane which transports said liquid more slowly than said fleece, wherein a portion of said porous membrane is in said detection zone and contains a reagent which forms a detectable signal with said analyte, wherein said porous membrane is in fluid contact with said fleece, said fluid contact permitting passage of liquid from said fleece to said porous membrane, said porous membrane being a membrane.

* * * * *